United States Patent [19]

Decke

[11] Patent Number: 5,617,027
[45] Date of Patent: Apr. 1, 1997

[54] LOCAL ANTENNA FOR NUCLEAR MAGNETIC RESONANCE DIAGNOSTICS

[75] Inventor: Guenther Decke, Hemhofen, Germany

[73] Assignee: Siemens Aktiengesellschaft, Munich, Germany

[21] Appl. No.: 613,723

[22] Filed: Mar. 12, 1996

[30] Foreign Application Priority Data

Mar. 13, 1995 [DE] Germany ............... 195 09 020.9

[51] Int. Cl.⁶ ....................................................... G01V 3/00
[52] U.S. Cl. .......................................... 324/318; 128/653.5
[58] Field of Search ............................... 324/318, 322, 324/307, 309, 314; 128/653.5

[56] References Cited

U.S. PATENT DOCUMENTS

| 4,887,038 | 12/1989 | Votruba et al. . | |
| 4,920,318 | 4/1990 | Misic et al. . | |
| 5,143,068 | 9/1992 | Muennemann et al. | 324/318 |
| 5,305,750 | 4/1994 | Makita . | |
| 5,379,768 | 1/1995 | Smalen | 324/318 |
| 5,400,787 | 3/1995 | Marandos | 324/318 |

FOREIGN PATENT DOCUMENTS

| 0304165 | 2/1989 | European Pat. Off. . |
| 0404592 | 6/1990 | European Pat. Off. . |
| 2238961 | 2/1974 | Germany . |
| 3826704 | 2/1990 | Germany . |
| 3827981 | 2/1990 | Germany . |

*Primary Examiner*—Louis M. Arana
*Attorney, Agent, or Firm*—Hill, Steadman & Simpson

[57] ABSTRACT

A local antenna for nuclear magnetic resonance diagnostics has a flexible antenna conductor arrangement. The antenna conductor arrangement forms a structural unit with a vacuum pillow.

8 Claims, 1 Drawing Sheet

LOCAL ANTENNA FOR NUCLEAR MAGNETIC RESONANCE DIAGNOSTICS

BACKGROUND OF THE INVENTION

1. Field of the Invention

The present invention is directed to a local antenna for nuclear magnetic resonance diagnostics having a flexible antenna conductor arrangement.

2. Description of the Prior Art

A local antenna of the general type described above is known from U.S. Pat. No. 4,920,318. This local antenna has a flexible plastic carrier to which one or several conductor loops are attached. The local antenna is arranged annularly around a region being examined during the examination and is then fastened using Velcro® straps. An impedance matching circuit or a tuning circuit is additionally arranged on the carrier.

During the examination—in particular ford orthopedic examinations—the patient or the region of the body to be examined must be immovably and comfortably positioned in order to avoid motion artifacts. The stable positioning can be supported by additional pillows and positioning cushions, however, this requires preparation time and thus increases measurement time. Moreover, different pillows and cushions must be kept available, from which a suitable one can be chosen as needed.

SUMMARY OF THE INVENTION

It is an object of the present invention to provide a local antenna that can be precisely positioned and with which at the same time a stable and comfortable positioning of the region of the body to be investigated is possible.

The above object is achieved in a local antenna wherein the antenna conductor forms a structural unit with a vacuum pillow. The local antenna can thereby be adapted to the shape of the body as well as to the shape of the patient bed. During examinations of joints in particular, the patient's comfort is increased, with a simultaneous improvement in image quality due to fewer motion artifacts. In addition, a shorter preparation time for the nuclear magnetic resonance examination results.

DESCRIPTION OF THE PREFERRED EMBODIMENTS

Figure 1:
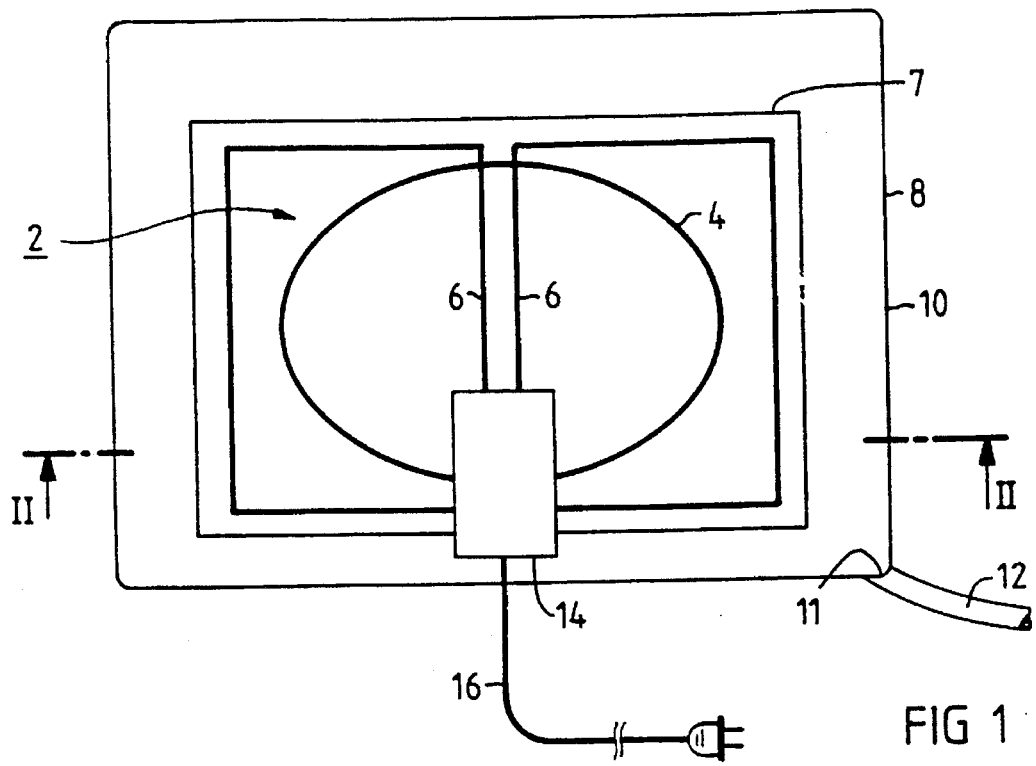
FIG. 1 is a top view of a local antenna constructed in accordance with the principles of the present invention.

The top view of a local antenna shown in FIG. 1 shows a circularly polarizing antenna conductor arrangement 2 arranged in a plane. The antenna conductor arrangement 2 has a first elliptical conductor loop 4 whose transmission/reception pattern maximum characteristic is essentially oriented perpendicularly to the surface. The antenna conductor arrangement 2 further has two rectangular conductor loops 6 arranged alongside one another, arranged symmetrically about the conductor loop 4. The two conductor loops 6 are activated in opposition, so that their combined transmission/reception pattern maximum is directed perpendicularly to that of the conductor loop 4 in an imaging region outside the surface of the antenna conductor arrangement 2. The antenna conductor arrangement 2 is made of a flexible material such as e.g. a copper foil fastened to a flexible carrier 7.

The antenna conductor arrangement 2 is attached to a surface of a vacuum pillow 8, however, the antenna conductor arrangement can also be inserted into a pocket in the vacuum pillow 8. The vacuum pillow 8 is somewhat larger than the antenna conductor arrangement 2, in order to ensure a good fixing of the antenna conductor arrangement 2 to the region to be examined. The vacuum pillow 8 has an airtight flexible sheath 10 with a connection 11 for a suction conduit 12.

An electronics box 14 also belongs to the structural unit of the antenna conductor arrangement 2 with the vacuum pillow 8, which contains a circuit for electrical matching and/or electrical tuning of the antenna conductor arrangement 2. The electrical connection of the antenna conductor arrangement 2 to an antenna feed line 16 ensues via the electronics box 14. The antenna conductor arrangement 2 and the electronics box 14 are provided with a cover (not shown in FIG. 1).

Figure 2:
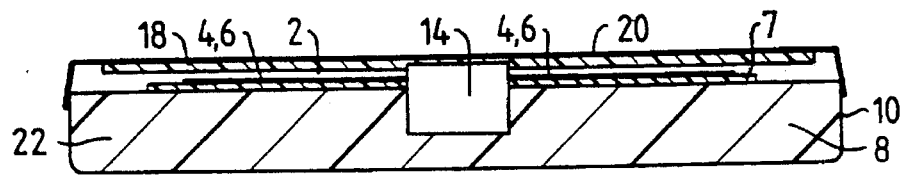
FIG. 2 a section through the local antenna of FIG. 1.

FIG. 2 shows a side view of a section through the local antenna, taken along line II—II in FIG. 1, but including the cover for the antenna conductor arrangement 2. The side of the antenna conductor arrangement 2 faced away from the vacuum pillow 8 is covered with a thin elastic layer 18. This elastic layer consists e.g. of a plate of foam material that serves as padding for a small space between the patient and the antenna conductor arrangement 2. The foam material plate 18 is covered with a protective film 20 that is easy to clean. The elastic sheath 10 of the vacuum pillow 8 is filled with small polystyrene balls 22. The vacuum pillow 8 is constructed to be voluminous enough so that the electronics box 14 can also be housed therein.

Figure 3:
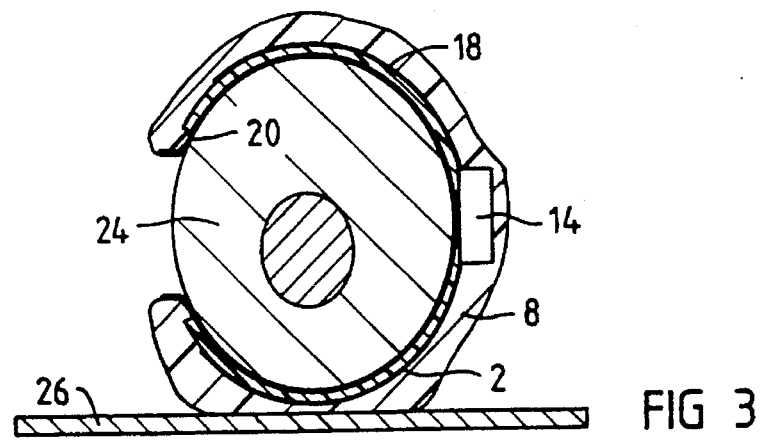
FIG. 3 the local antenna in use for conducting an examination of a thigh.

FIG. 3 shows the local antenna in use for the examination of a thigh 24. The thigh 24 is represented in cross-section. The local antenna 24 is wrapped around the thigh 24 before the examination. The subsequent evacuation of the vacuum pillow 8 via the suction conduit 12 causes the antenna conductor arrangement 2 to adapt itself to the surface of the region to be examined and to be fixed in conformity with the surface, and simultaneously ensures a stable and comfortable positioning of the thigh 24 on a patient bed 26.

Although modifications and changes may be suggested by those skilled in the art, it is the intention of the inventor to embody within the patent warranted hereon all changes and modifications as reasonably and properly come within the scope of his contribution to the art.

I claim as my invention:

1. A local antenna for nuclear magnetic resonance diagnostics comprising:

a vacuum pillow having an air tight sheath with a connection for a suction conduit;

a plurality of solid plastic balls filling said sheath; and a flexible antenna conductor arrangement forming a structural unit with said vacuum pillow.

2. A local antenna as claimed in claim 1 wherein said antenna conductor arrangement is disposed on a surface of said vacuum pillow.

3. A local antenna as claimed in claim 2 further comprising an elastic layer covering said antenna conductor arrangement on a side of said antenna conductor arrangement faced away from said vacuum pillow.

4. A local antenna as claimed in claim 1 wherein said solid plastic balls comprise polystyrene balls.

5. A local antenna as claimed in claim 1 wherein said antenna conductor arrangement comprises a circularly polarizing antenna conductor arrangement.

6. A local antenna as claimed in claim 1 further comprising, as part of said structural unit, electrical means for matching said antenna conductor arrangement.

7. A local antenna as claimed in claim 1 further comprising, as part of said structural unit, electrical means for tuning said antenna conductor arrangement.

8. A local antenna as claimed in claim 1 further comprising, as part of said structural unit, electrical means for matching and tuning said antenna conductor arrangement.

* * * * *